United States Patent [19]

Myers et al.

[11] Patent Number: 6,040,334

[45] Date of Patent: Mar. 21, 2000

[54] USE OF INHIBITORS OF 3-HYDROXY-3-METHYLGLUTARYL COENZYME A REDUCTASE AS A MODALITY IN CANCER THERAPY

[75] Inventors: Charles Myers, Rockville; Jane Trepel, Bethesda; Won Ki Kang, Rockville; Luke Whitesell; Len Neckers, both of Bethesda, all of Md.

[73] Assignee: The United States of America as represented by the Secretary of the Department of Health and Human Services, Washington, D.C.

[21] Appl. No.: 08/330,865

[22] Filed: Oct. 20, 1994

Related U.S. Application Data

[63] Continuation of application No. 07/882,223, May 13, 1992, abandoned.

[51] Int. Cl.$^7$ .................................................. A61K 31/35
[52] U.S. Cl. ............................................................ 514/460
[58] Field of Search ............................................. 514/460

[56] References Cited

U.S. PATENT DOCUMENTS

| | | | |
|---|---|---|---|
| 5,130,333 | 7/1992 | Pan et al. | 514/460 |
| 5,595,734 | 1/1997 | Mikulski et al. | 514/183 |

OTHER PUBLICATIONS

Week 8143, Derwent Publications Ltd, London, GB; AN 81–78653D & JP–A–56115717 (Endo, Akira) Sep. 11, 1981 (D4) discloses the prevention of hypertrophy by oral administration of monacolin K or ML–236B or derivatives thereof in a dosage of 0.5–1000 mg/kg/day.

Kort, W.J., et al. *Clin. Expl. Metastasis* 7:517 (1989).

Kelloff, G.J., et al. *Journal of Cellular Biochemistry*, Supp. 16H:1 (1992).

Mikulski, S.M., et al. *Br. J. Cancer* 66:304 (1992).

Soma, M.R., et al. *Cancer Research* 52:4348 (1992).

Sumi, S., et al. *Gastroenterology* 103:982 (1992).

Maltese, W.A., et al. *Neurology* 33:1294 (1983).

Thibault, A., et al. *Clinical Cancer Research* 2:483 (1996).

Duggan and Vickers, "Physiological Disposition of HMG–CoA–Reductase Inhibitors," *Drug Metabolism Reviews*, vol. 22, No. 4 (1990), pp. 333–362.

Sebti, et al., "Lovastatin, a Cholesterol Biosynthesis Inhibitor, Inhibits the Growth of Human H–ras Oncogene Transformed Cells in Nude Mice," *Cancer Communications*, vol. 3, No. 5 (1991), pp. 141–147.

Maltese, et al., "Suppression of Murine Neuroblastoma Growth Methylglutaryl–Coenzyme A Reductase," *Journal of Clinical Investigation*, vol. 76 (Nov. 1985), pp. 1748–1754.

Keyomarsi, et al., "Synchronization of Tumor and Normal Cells from $G_1$ to Multiple Cell Cycles by Lovastatin," *Cancer Research*, vol. 51 (Jul. 1, 1991), pp. 3602–3609.

Mantell, et al., "Extended Clinical Safety Profile of Lovastatin," *The American Journal of Cardiology*, vol. 66, (Sep. 18, 1990), pp. 11B–15B.

Jakóbisiak, et al., "Cell cycle–specific effects of lovastatin," *Proc. Natl. Acad. Sci. USA*, vol. 88 (May 1991), pp. 3628–3632.

Sepp–Lorenzino, et al., "Cellular distribution of cholesterogenesis–linked, phospho–isoprenylated proteins in proliferating cells," *F.E.B.S. Letters*, vol. 245, Nos. 1–2 (Mar. 1989), pp. 110–166.

Maltese and Sheridan, "Isoprenylated Proteins in Cultured Cells: Subcellular Distribution and Changes Related to Altered Morphology and Growth Arrest Induced by Mevalonate Deprivation," *Journal of Cellular Physiology*, vol. 133 (1987), pp. 471–481.

MacDonald, et al., "Preclinical Evaluation of Lovastatin," *The American Journal of Cardiology*, vol. 62 (Nov. 11, 1988), pp. 16J–27J.

Larsson, et al., "Abolition of Mevinolin–induced Growth Inhibition in Human Fibroblasts following Transformation by Simian Virus 40," *Cancer Research*, vol. 49 (Oct. 15, 1989), pp. 5605–5610.

Larsson, "Role of Biosynthesis of Cholesterol and Isoprenoid Derivatives in Regulation of $G_1$ Progression and Cell Proliferation of 3T6 Cells," *Journal of Cellular Physiology*, vol. 133 (1987), pp. 163–168.

Fairbanks, et al., "Effects of Mevinolin and Mevalonate on Cell Growth in Several Transformed Cell Lines," *Journal of Cellular Physiology*, vol. 127 (1986), pp. 216–222.

Dujovne, et al., "Expanded Clinical Evaluation of Lovastatin (EXCEL) Study Results: IV. Additional Perspectives on the Tolerability of Lovastatin," *The American Journal of Medicine*, vol. 91 (suppl. 1B) (Jul. 31, 1991) pp. 1B–25S—1B–30S.

DeClue, et al., "Inhibition of Cell Growth by Lovastatin Is Independent of ras Function," *Cancer Research*, vol. 51 (Jan. 15, 1991), pp. 712–717.

Bradford, et al., "Expanded Clinical Evaluation of Lovastatin (EXCEL) Study Results: III. Efficacy in Modifying Lipoproteins and Implications for Managing Patients with Moderate Hypercholesterolemia," *The American Journal of Medicine*, vol. 91 (suppl. 1B) (Jul. 31, 1991), pp. 1B–18S–1B–24S.

Bradford, et al., "Expanded Clinical Evaluation of Lovastatin (EXCEL) Study: Design and Patient Characteristics of a Double–Blind, Placebo–Controlled Study in Patients with Moderate Hypercholesterolemia," *The American Journal of Cardiology*, vol. 66 (Sep. 18, 1990), pp. 44B–55B.

(List continued on next page.)

*Primary Examiner*—Jerome D. Goldberg
*Attorney, Agent, or Firm*—Townsend and Townsend and Crew LLP

[57] ABSTRACT

Methods of treating various cancers, such as prostatic adenocarcinoma, with inhibitors of 3-hydroxy-3-methylglutaryl coenzyme A reductase (HMG Co-A), such as lovastatin, are provided. Dosing ranges, schedules and toxicities are included.

5 Claims, 3 Drawing Sheets

OTHER PUBLICATIONS

Bradford, et al., "I. Efficacy in Modifying Plasma Lipoproteins and Adverse Event Profile in 8245 Patients With Moderate Hypercholesterolemia," *Arch. Intern. Med.*, vol. 151 (Jan. 1991), pp. 43–49.

Bansal, et al., "Apoptosis: mode of cell death induced in T cell leukemia lines by dexamethasone and other agents," *The F.A.S.E.B. Journal*, vol. 5 (Feb. 1991), pp. 212.

Alberts, "Discovery, Biochemistry and Biology of Lovastatin," *The American Journal of Cardiology*, vol. 62 (1988), pp. 10J–15J.

USE OF INHIBITORS OF 3-HYDROXY-3-METHYLGLUTARYL COENZYME A REDUCTASE AS A MODALITY IN CANCER THERAPY

This is a Continuation of application Ser. No. 07/882,223, filed May 13, 1992, now abandoned.

BACKGROUND OF THE INVENTION

The invention relates generally to use of inhibitors of 3-hydroxy-3-methylglutaryl coenzyme A reductase in treating cancer. More specifically the invention relates to use of lovastatin and its homologues or analogues to treat human adenocarcinoma and selected sarcomas.

Metastatic prostate cancer and stomach cancer are refractory to all available cytotoxic agents. There is no curative medical therapy for these common adult carcinomas. Lovastatin, widely used for treatment of hypercholesterolemia, is generally believed to be useful for synchronizing tumor cell growth in one cell cycle phase. Although there exist scattered reports of the cytotoxic activity of lovastatin, it has not been pursued as an anticancer drug.

Adenocarcinoma is a group in the histological classification of cancer. For instance, 95% of prostate carcinomas are adenocarcinomas. Cancers of the stomach, intestine and colon are almost always adenocarcinomas, as are gall bladder cancers. Breast cancer is also an adenocarcinoma in perhaps 90% of the cases. Cancer of the esophagus is adenocarcinoma in about 10%–15% of cases and adenocarcinoma of the lung represents about 30% of pulmonary cancers.

One of the challenges in treating cancer is the ability to follow the course of the disease and the efficacy of therapy with some objective marker. Ideally, the marker would be obtainable by either noninvasive or minimally invasive means such as a blood test. The marker may be useful in diagnosing a type of cancer as well as in evaluating the prescribed therapy.

An example of a tumor marker is prostate specific antigen (PSA). Serum PSA is clinically useful to monitor the therapeutic response of prostatic cancer patients. See Hudson et al., Clinical Use of Prostate Specific Antigen in Patients With Prostate Cancer, *Journal of Urology* 142:1011–1017 (October 1989).

Inhibitors of 3-hydroxy-3-methylglutaryl coenzyme A reductase (HMG Co-A) are known. HMG Co-A catalyzes a crucial step in the biosynthesis of cholesterol. Inhibitors of this enzyme are well known as cholesterol lowering agents. See U.S. Pat. No. 3,983,140 to Endo et al which is incorporated by reference herein. Examples of these inhibitors include the group of physiologic active substances ML-236. Compactin (ML-236B) is a member of this group, and it has been isolated from cultures of *Penicillium brevicompatum* and *Penicillium citrinum*. See '140 to Endo et al. See also Brown et al, Crystal and Molecular Structure of Compactin, a New Antifungal Metabolite From *Penicillium Brevicompatum*, *Journal Chemical Society Perkins Trans.* I 1165–1170 (1976).

The structures of compactin and some of its homologues are well characterized, and their total synthesis has been achieved by a number of groups. See for example Grieco et al, Total Synthesis of the Hypocholesterolemic Agent Compactin, *Journal American Chemical Society* 105:1403–1404 (1983), Wang et al, Total Synthesis of Compactin (ML-236B), *Journal American Chemical Society* 103:6538–6539 (1981), and Hsu et al, Total Synthesis of the Hypocholesterolemic Agent Compactin, *Journal American Chemical Society* 105:593–601 (1983).

The structural formula of some of the known inhibitors of HMG Co-A is represented by formula I

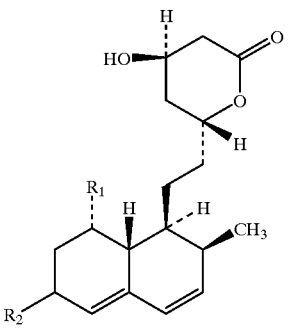

wherein $R^1$ is a hydrogen atom, a hydroxy group, a 2-methylbutyryloxy group (—OCOCH($CH_3$)$CH_2CH_3$) or a 2,2-dimethylbutyryloxy group (—OCOC($CH_3$)$_2CH_2CH_3$) and $R_2$ is a hydrogen atom or a methyl group. In lovastatin, $R_1$ is a 2-methylbutyryloxy group and $R_2$ is a methyl group. In the compound mevastatin, $R_1$ is a methyl group and $R_2$ is a hydrogen atom. Simvastatin has a 2,2-dimethylbutyryloxy group in the $R_1$ position and a methyl group in the $R_2$ position.

A number of therapeutic measures, such as surgical excision, chemotherapy and radiation, are available in cancer therapy. Frequently, a combination regimen using more than one of the above-mentioned modalities is employed. Additionally, an array of chemotherapeutic agents may be used in treating any one cancer patient. If a tumor marker is available, then knowledge of its abundance may help the clinician tailor the therapeutic regimen. For example, if a patient suffering from prostatic carcinoma receives a drug which lowers his PSA, then the clinician may conclude that the tumor is regressing. Thus, he will alter the patient's therapy accordingly.

SUMMARY OF THE INVENTION

The invention provides a method for treating mammalian adenocarcinomas and sarcomas comprising administration of an effective amount of an inhibitor of HMG Co-A or homologues of the inhibitor. Adenocarcinoma is known to afflict the prostate, stomach, lung, breasts and colon, as well as other sites. An example of a sarcoma within the meaning of the present invention is Ewing's sarcoma, which is a medullary bone tumor typically attacking the long bones.

"Homologue(s)" refers to compounds of similar chemical structure but which have different radicals or side groups substituted. The term is further meant to include analogues or compounds with similar electronic structures but different atoms; isolog is a synonym. When referring to treating a cancer, improved or decreased symptoms are included. That is, "treatment" is not limited to an objective regression of tumor size, but also includes the patient's report of his subjective status.

An effective amount of the compound is that amount which provides either subjective relief of symptoms or decrease in the tumor burden or decrease in an identifiable tumor marker. Administration of the compound is by any medically or pharmaceutically accepted route. Typically, the oral route is preferred. The dosing range is preferably from about 2.0 to about 52.0 mg/kg/day based on the patient's body weight. More specifically, the range is from about 6.0 to about 36.0 mg/kg/day.

Examples of compounds useful in the present invention are lovastatin and simvastatin as well as their homologues. Also included are compounds classified as HMG Co-A inhibitors, as well as their homologues or analogues. Generally, these HMG Co-A inhibitors are known to lower serum cholesterol in humans. However, the present invention is not so limited. That is, an inhibitor of HMG Co-A or one of its homologues may work in the method of the present invention without necessarily lowering serum cholesterol. The invention focuses not on the compound's ability to lower cholesterol, but rather on the compound's ability to treat selected cancers, such as adenocarcinomas of the prostate, stomach, lung, breast and colon and certain sarcomas such as Ewing's sarcoma.

Also provided by the invention is a method of reducing PSA levels in a patient having prostatic adenocarcinoma comprising administration of an effective amount of a compound which is an inhibitor of HMG Co-A or a homologue or analogue of such an inhibitor. The invention also includes a method of reducing PSA in conjunction with another treatment modality. Additionally described is an appropriate unit dose ranging from about 100 mg to about 2000 mg.

DESCRIPTION OF THE PREFERRED EMBODIMENT

Figure 1:
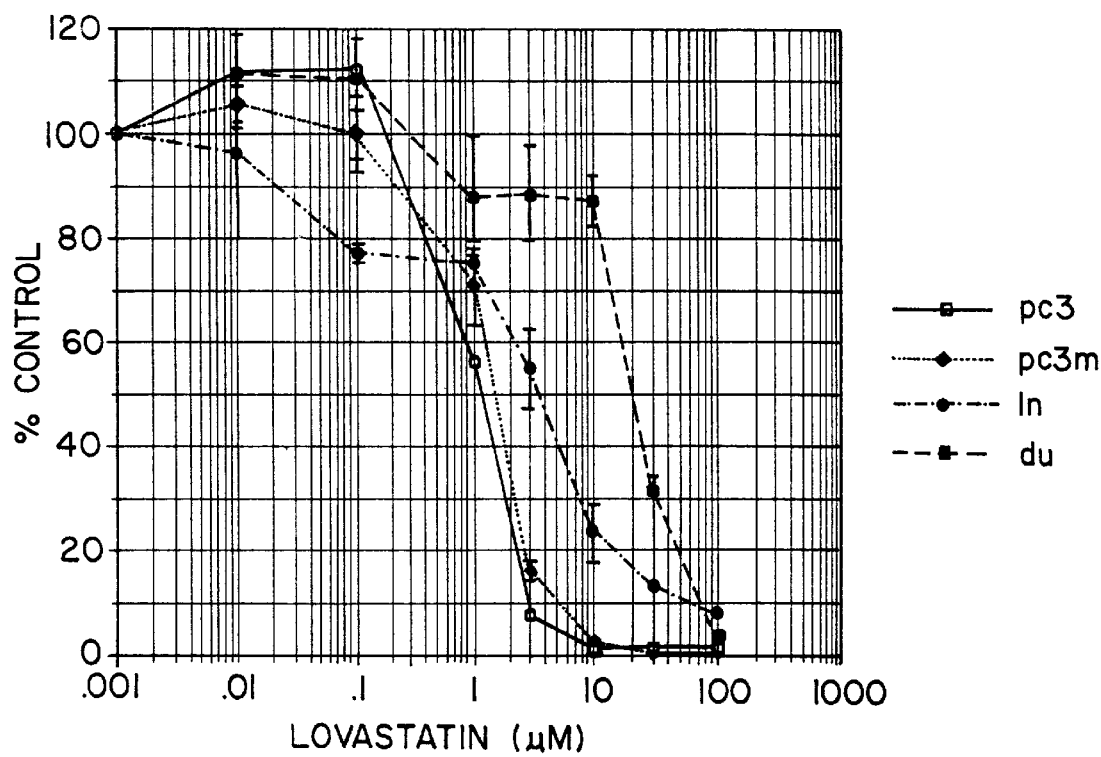
FIG. 1 is a graph of concentration-dependence of lovastatin-induced growth arrest in human prostate cancer cell lines.

Lovastatin induces cell death of certain susceptible human tumor types in vitro in a dose achievable in vivo. Clinical data presented here demonstrate anti-cancer activity of short course, high dose lovastatin as measured by decline in the level of the tumor marker PSA in patients with prostate cancer.

Data collected thus far indicate that patients with prostate cancer, both hormone-refractory and hormone-sensitive, and patients with gastric cancer are good candidates for the cytotoxic activity of lovastatin and related compounds. In addition, certain patients with breast cancer, Ewing's sarcoma, and other selected tumors respond to the anti-cancer activity of this class of drugs. In vitro testing is currently underway to facilitate selection of patients.

Lovastatin rapidly acts on the human prostatic carcinoma cell lines, PC-3, PC-3-M, DU-145 and LNCaP, and the LD 50s were all below 10 µg/ml for exposures of 4 days. In the case of PC-3-M, there was complete loss of clonogenicity after exposure to 4 µg/ml for 4 days. The term "clonogenicity", or immortality, refers to the ability of an isolated cell to produce progeny in vitro. Thus, in the case of human prostate cancer, rapid tumor cell kill may be seen at blood levels which animal models and studies in human cancer patients suggest are tolerable in humans.

Dose and Schedule

In mammalian cells, lovastatin acts to arrest growth, not to kill cells, at drug levels as high as 100 times that currently used in patients. In the present invention, the currently approved hypercholesterolemic drug lovastatin is self-administered orally four times a day for seven days every 28 days. Initial doses start at about 2 to 4 mg/kg/day. The clinical indication, dosage and schedule differ from the current use of this drug and other drugs in this class.

The conventional clinical dosage for hypercholesterolemia ranges from 20–80 mg per day. With conventional management, lovastatin dose is not modified according to body weight or surface area. However, to use the present invention, the dose is adjusted based on body size, and 2 mg/kg/day (0.5 mg/kg QID, where "QID" means "four times a day") is a preferred starting dose. Alternatively, other schedules, such as TID (three times a day) or BID (twice a day) could be employed.

In the original clinical development of this drug, there were no phase 1 studies to determine dose-limiting toxicity in patients. With the doses in current clinical use, toxicities with potentially serious outcome are ordinarily limited to rhabdomyolysis and liver injury. The frequency of each of these toxicities is less than 1.5% at the currently recommended doses. In vitro studies have shown inhibition of lymphocyte proliferation at drug levels targeted by the phase 1 study described below.

To practice the invention, oral administration is preferred. An effective quantity of HMG Co-A inhibitor or related compound is employed in treatment. The dosage of the specific compound for treatment depends on many factors that are well known to those skilled in the art. They include for example, the route of administration and the potency of the particular compound. A preferred dosage for humans of about 70 kgs is from about 35 mg to about 910 mg in a single dose taken four times a day. Generally the dose is from about 2 to about 52 mg per kg per day.

A preferred dosing schedule is an oral dose usually four times a day for a limited period, typically about 7 days. The schedule is preferably repeated at a suitable interval, usually at about 28-days with the first day of the first cycle counted as day one.

Recognized Toxicities of Lovastatin and Their Management

1. Hepatic Toxicity

Oral administration ensures high hepatic drug levels. In addition, the liver is a major site of lovastatin activation from the lactone to the more active acid form. Most of the drug is cleared by hepatic metabolism and biliary secretion. Also, the liver is the major site of cholesterol synthesis and thus the site at which lovastatin accomplishes most of its effect upon circulating cholesterol levels. Lovastatin can cause hepatocellular injury, but this is usually very limited in severity.

At the dose range given for hyperlipidemia (maximum of 80 mg/day), approximately 1.5% of patients will experience a three-fold rise in hepatic transaminase levels. In all cases, hepatic transaminase levels returned to normal within several weeks of discontinuation of lovastatin therapy.

2. Rhabdomyolysis

Muscle pain associated with elevated creatine phosphokinase (CPK) levels have been reported. At a dose of 80 mg/Day, about 1.5% of patients will experience CPK elevations of >1,000 U/L (5 times normal). Clinically evident myopathy associated with prolonged elevation of CPK and muscle discomfort has been seen in less than 0.1% of cases.

3. Lens Opacities

The development of lens opacities during the course of lovastatin therapy have been reported. However, these changes also occur spontaneously in this age group and at present blinded, randomized trials do not support an increased risk in patients on recommended doses of lovastatin. Nevertheless, this side effect may emerge as significant with dose escalation.

4. Idiosyncratic Reactions

Lovastatin has been on the market for several years and more than one million patients have been treated with it. During that time, a number of reactions have been reported in one or a few patients that were not seen in preclinical testing or in the extensive clinical trials that preceded marketing approval. These have been so uncommon that the relationship of these reactions to lovastatin is at present unclear.

However, as the dose is escalated in practicing this invention, one or more of these rare events may occur with greater consistency. They include: alopecia, depression, bleeding, skin rash, anaphylaxis, arthralgia, Lupus-like syndrome, angioedema, urticaria, hemolytic anemia, leucopenia, and thrombocytopenia.

5. Preclinical Toxicities not Noted in Patients at Conventional Doses

In rabbits, but not mouse, rat, dog or monkey, lovastatin causes renal failure at peak blood levels of 8–10 $\mu$g/ml. In rabbits, but not mouse, dog or monkey, lovastatin causes gallbladder necrosis. In dogs, but not mouse, rat, rabbit or monkey, lovastatin can cause testicular atrophy. In rat and mouse, lovastatin causes lesions in the nonglandular stomach which is a non-acid producing portion of an animal's stomach, presumably used to store food. Since humans do not have an equivalent of the nonglandular stomach, the relevance of this observation is not known.

Therapeutic Administration

Lovastatin is approved for marketing in the U.S. and is currently one of the top ten drugs prescribed in the clinical setting. It is available as both 20 and 40 mg tablets for oral administration. As excipients, each tablet contains cellulose, lactose, magnesium stearate and starch. The 20 mg tablets contain FD & C blue dye number 2. The 40 mg tablet is green and contains both FD&C blue dye number 2 and yellow dye number 10. Tablets should be stored between 2 and 30° C., protected from light, and kept in a well-closed container. Simvastatin, recently been approved in the United States to treat elevated cholesterol, is represented by formula II

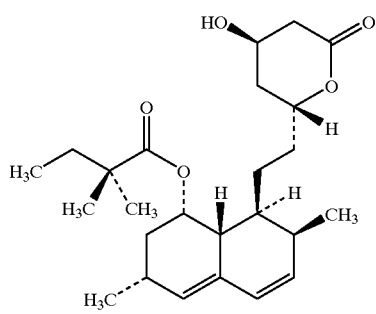

Compositions of the present invention are presented for administration to humans and animals in unit dosage forms, such as tablets, capsules, pills, powders, granules, eye drops, oral solutions or suspensions and water-in-oil emulsions containing suitable quantities or formulations of HMG Co-A inhibitors.

For oral administration, either solid or fluid unit dosage forms can be prepared. For preparing solid compositions such as tablets, HMG Co-A inhibitors are mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers.

Capsules are prepared by mixing the inhibitor or related compound with an inert pharmaceutical diluent and filling the mixture into hard gelatin capsule of appropriate size. Soft gelatin capsules are prepared by machine encapsulation of a slurry of the inhibitor or related compound with an acceptable vegetable oil, light liquid petrolatum or other inert oil.

Fluid unit dosage forms for oral administration such syrups, elixirs and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. Some examples of suitable unit dosage forms are tablets, capsules, pills, powder packets, wafers, granules, teaspoonfuls, tablespoonfuls, droppersful, ampoules, and vials.

The following examples are illustrative, and not limitations of the invention. Those skilled in the art will promptly recognize appropriate variations from the procedures as to dosing, scheduling, indications and toxicity.

EXAMPLES

Example 1

Cell lines of human prostate cancer cells were cultivated using methods well known to those of ordinary skill in the art. Varying doses of lovastatin from 0.001 to 100 micromoles per liter ($\mu$M) were administered to four such cell lines and compared against control cell lines. Of the experimental cell lines, three were hormone-independent (PC-3, PC-3-M, and DU 145) and one was hormone-sensitive (LNCaP). All four prostate cancer cell lines responded to lovastatin at doses from 1 to 100 $\mu$M compared to controls. The response of the treated cancer cells did not correlate with hormone sensitivity of the cancer cells. See FIG. 1.

Example 2

Figure 2:
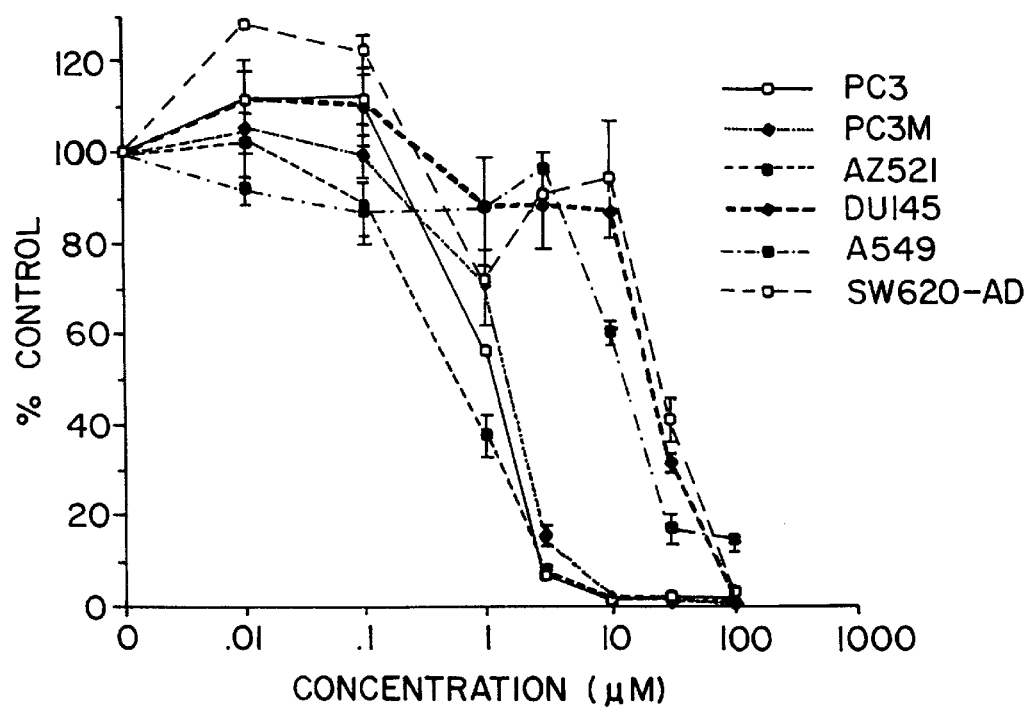
FIG. 2 is a graph of concentration-dependence of lovastatin-induced growth arrest in six defined human solid tumors in cell lines.
Figure 3:
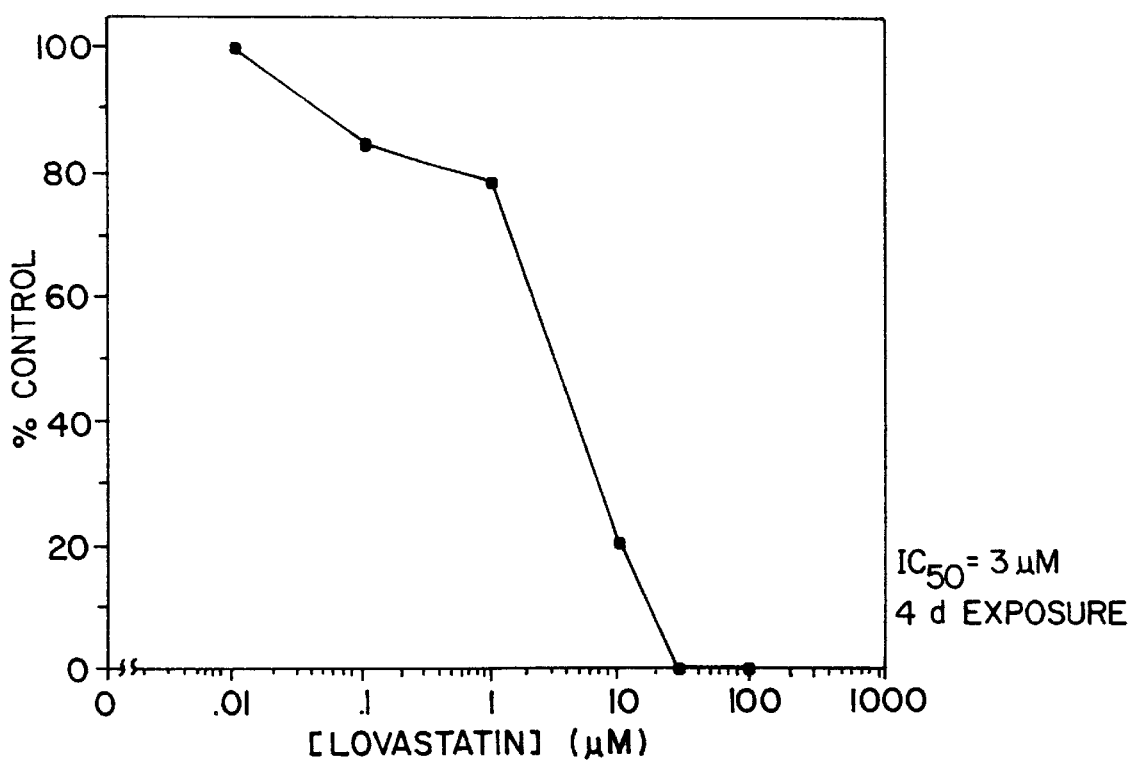
FIG. 3 is a graph of concentration-dependence of lovastatin-induced loss of clonogenicity in a human prostate carcinoma cell line.

Various human cell lines were cultivated using techniques well known to those of ordinary skill in the art. These cell lines were derived from cells of prostate carcinoma (PC-3/PC-3-M/DU 145), stomach cancer (AZ 521), pulmonary adenocarcinoma (A 549) and colon carcinoma (SW 620-AD). Concentrations of lovastatin varying from 0.01 to 100 $\mu$M were applied to each of the six cell lines and the response was compared to the controls as a percentage of growth. See FIG. 2. The data show good response to lovastatin dosages of 1 to 100 μM. Thus, various adenocarcinomas are sensitive to lovastatin treatment.

Example 3

To demonstrate loss of clonogenicity in a cancer cell line, a human prostate carcinoma cell line (PC-3-M) was treated with doses of lovastatin varying from 0.5 to 100 μM and compared against controls as a percentage of growth. The data indicate some loss of clonogenicity when the lovastatin dose was from 0.1 to 1 μM and an extreme loss of clonogenicity at 10 μM with absence of clonogenicity at dosages of 40 to 100 μM. The exposure of the cell lines to lovastatin occurred over a four day period.

Example 4

Figure 4:
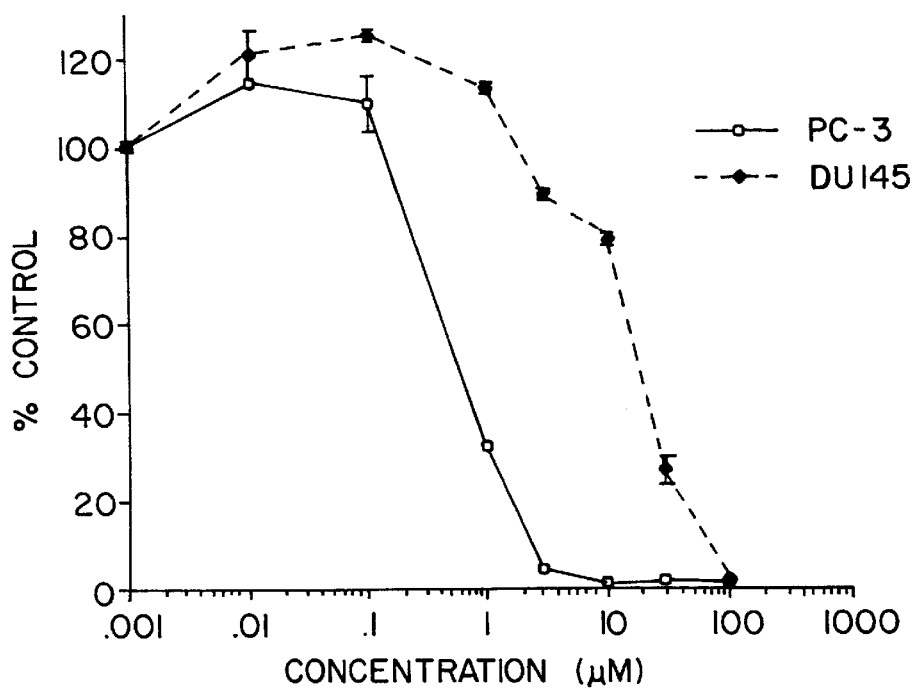
FIG. 4 is a graph of concentration-dependent growth arrest following treatment of two human prostate carcinoma cell lines with simvastatin.

Two human prostate carcinoma cell lines, PC-3 and DU 145, were treated with simvastatin, a lovastatin analogue which is also a product of Merck & Co. The concentration of simvastatin varied from 0.5 to 100 μM. The growth of the cancer cell lines was compared to control cell lines as a percentage. The data indicate that at concentrations of 1 to 100 μM of simvastatin, the cancer cell growth diminished substantially with both cell lines showing essentially zero growth after treatment with 100 μM of simvastatin. See FIG. 4.

Example 5

Figure 5:
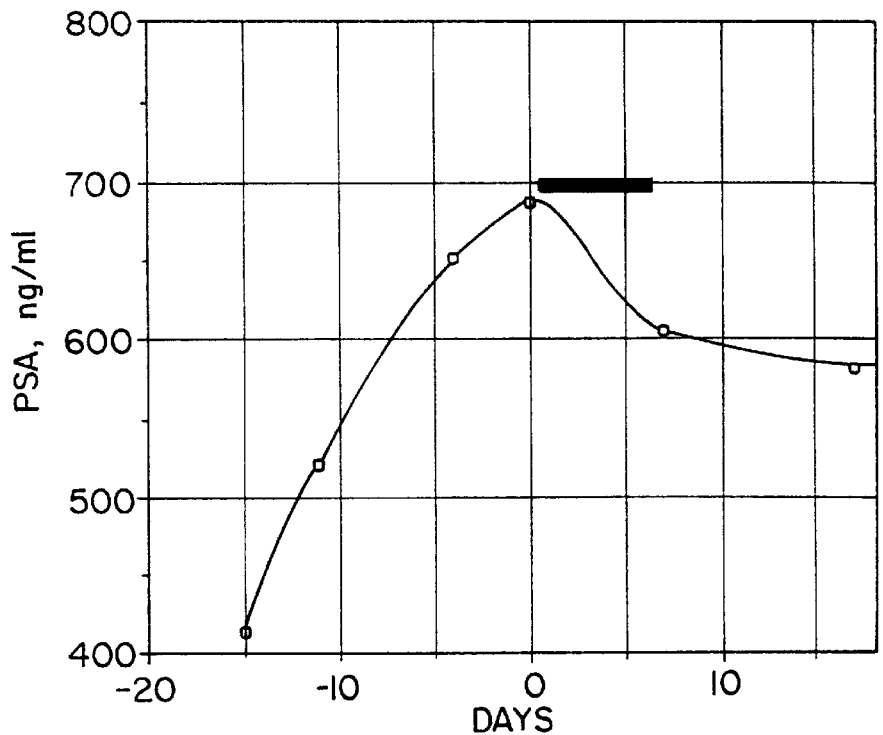
FIG. 5 is a graph of effect of lovastatin on plasma PSA level in a patient treated at 2 mg/kg/day for 7 days.

In a clinical trial, a patient having prostatic adenocarcinoma was treated with 2 mg/kg/day of lovastatin administered orally daily for 7 days. The patient's plasma PSA levels were determined. Pretreatment PSAs show an exponential increase. At the time of drug administration, the patient's blood level of PSA was approximately 700 nanograms per milliliter (ng/ml). After 7 days of treatment, the PSA had diminished to 600 ng/ml where it remained when tested on day 17 after treatment. See FIG. 5. A heavy bar shows the time interval of drug administration.

Example 6

Figure 6:
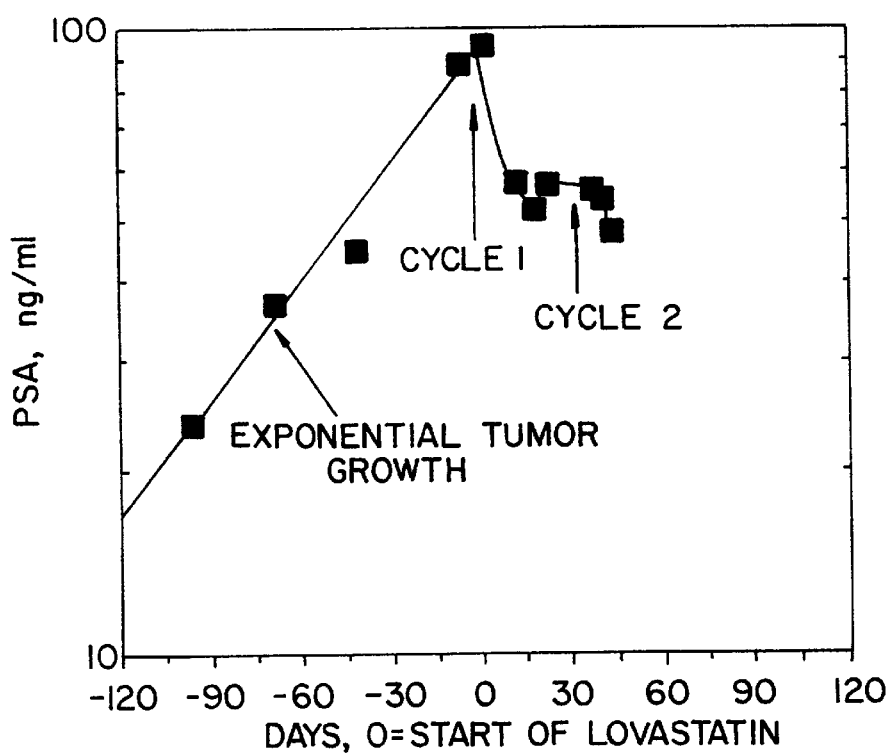
FIG. 6 is a graph of effect of lovastatin on plasma PSA level in a patient treated for 2 cycles at 2 mg/kg/day/7 days.

In a clinical trial, a patient having prostatic adenocarcinoma was treated for two cycles at 2 mg/kg/day for 7 days with the second cycle occurring 28 days later. The patient's plasma PSA levels were determined. The pretreatment PSA levels show an exponential increase from approximately 120 pretreatment until the treatment day. On the first day of treatment, the patient's PSA level was approximately 100 ng/ml. After the first cycle or 7 days of treatment, the patient's PSA level diminished to about 55 to 60 ng/ml. See FIG. 6.

Example 7

A Phase 1 Clinical Trial of short course, high dose lovastatin in the treatment of patients with cancer for whom there are no other therapeutic options of proven effectiveness is in progress.

The starting dose is 2 mg/kg/day (0.5 mg/kg QID). The dose is escalated to 25.8 mg/kg/day. Each escalation is fixed at 2 mg/kg/day until a dose of 3 mg/kg QID is reached, after which the dose increases by 20% increments.

Dose escalation is monitored primarily with a series of pharmacodynamic parameters as well as toxicity signs and symptoms. Because this is a phase 1 trial, it is open to patients with any malignancy.

The lovastatin is administered QID for seven consecutive days. During the first week of the first cycle, patients are carefully monitored as outpatients. Therapy is repeated after a three week (21 day rest). Such 28 day cycles may be repeated until tumor progression has been documented or CTEP grade III or greater toxicity prevents further treatment. CTEP stands for Cancer Therapy Evaluation Program which those in the art recognize as a program under the National Cancer Institute that controls clinical trials.

A minimum of three patients are treated at each dose level and followed for one month before moving to the next dose level. Doses are based upon actual body weight.

|  | Dose per Kg/QID | (Total Dose per Day) | % increase in dose |
|---|---|---|---|
| Level 1 | 0.5 mg/Kg QID | (2.0 mg/Kg/Day) | — |
| Level 2 | 1.0 mg/Kg QID | (4.0 mg/Kg/Day) | 100 |
| Level 3 | 1.5 mg/Kg QID | (6.0 mg/Kg/Day) | 50 |
| Level 4 | 2.0 mg/Kg QID | (8.0 mg/Kg/Day) | 33 |
| Level 5 | 2.5 mg/Kg QID | (10.0 mg/Kg/Day) | 25 |
| Level 6 | 3.0 mg/Kg QID | (12.0 mg/Kg/Day) | 20 |
| Level 7 | 3.6 mg/Kg QID | (14.4 mg/Kg/Day) | 20 |
| Level 8 | 4.3 mg/Kg QID | (17.2 mg/Kg/Day) | 20 |
| Level 9 | 5.15 mg/Kg QID | (20.6 mg/Kg/Day) | 20 |
| Level 10 | 6.2 mg/Kg QID | (24.8 mg/Kg/Day) | 20 |
| Level 11 | 14.9 mg/Kg QID | (29.8 mg/Kg/Day) | 20 |
| Level 12 | 8.95 mg/Kg QID | (35.8 mg/Kg/Day) | 20 |
| Level 13 | 10.75 mg/Kg QID | (43.0 mg/Kg/Day) | 20 |
| Level 14 | 12.9 mg/Kg QID | (51.8 mg/Kg/Day) | 20 |

Because lovastatin is available in 20 and 40 mg tablets, the dose is rounded off to the nearest multiple of 20 mg. If, at any dose level, one patient develops CTEP grade III toxicity, then additional patients are entered at that dose level until at least 6 patients have been treated. If grade III or higher toxicity develops in 3 of the 6 patients entered at any given dose level, then no further dose escalation is be made and the next lower lovastatin dose will be considered to be a maximally tolerated dose, and an additional three patients entered at this dose to confirm that it is safe. If a patient experiences a grade III toxicity but is responding to therapy, he may be retreated at the next lower dose level. A maximum of 60 patients are placed on this trial.

CTEP common toxicity criteria do not exist for rhabdomyolysis. Thus, it is necessary to set separate criteria for this toxicity. For this purpose, an elevation of CPK to 10 times normal or muscle pain sufficient to make daily activities difficult are regarded as equivalent to a CTEP grade III toxicity.

As the dose levels escalate, patients who entered at lower dose levels may have their dose increased on their next cycle. The maximal dose allowed will be one dose level lower than the current dose level being investigated. Although a QID schedule is preferred, other schedules, such as TID or BID could be used.

What is claimed is:

1. A method for treating an adenocarcinoma selected from the group consisting of an adenocarcinoma of the prostate, an adenocarcinoma of the breast, an adenocarcinoma of the stomach, a pulmonary adenocarcinoma, and an adenocarcinoma of the colon in a mammal, comprising oral administration of an effective amount of a compound of the formula I

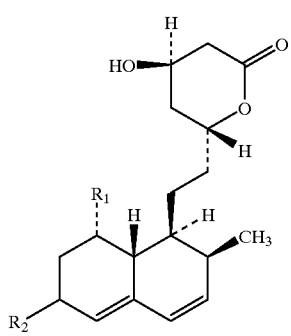

wherein $R_1$ is selected from a group consisting of a hydrogen atom, a hydroxy group, a 2-methylbutyryloxy group (—OCOCH($CH_3$)$CH_2CH_3$) and a 2,2-dimethylbutyryloxy group (—OCOC($CH_3$)$2CH_2CH_3$) and $R_2$ is selected from a group consisting of a hydrogen atom and a methyl group.

2. The method of claim 1 wherein the compound is chosen from the group comprising lovastatin and simvastatin.

3. The method of claim 1, wherein the adenocarcinoma is a hormone-responsive prostate adenocarcinoma.

4. The method of claim 1 wherein the effective amount is from about 2.0 to about 52.0 mg/kg/day.

5. The method of claim 4 wherein the effective amount is about 6.0 to 36.0 mg/kg/day.

* * * * *